US005521208A

United States Patent [19]
York

[11] Patent Number: 5,521,208
[45] Date of Patent: May 28, 1996

[54] COMPOSITIONS AND METHODS FOR THE TREATMENT OF THE METABOLICALLY IMPAIRED AND FOR IMPROVED COMPLIANCE

[75] Inventor: Billie M. York, Fort Worth, Tex.

[73] Assignee: Alcon Laboratories, Inc., Fort Worth, Tex.

[21] Appl. No.: 99,304

[22] Filed: Jul. 29, 1993

[51] Int. Cl.$^6$ ................................................. A61K 31/40
[52] U.S. Cl. ........................ 514/409; 514/866; 514/922
[58] Field of Search ................................. 514/866, 922, 514/409

[56] References Cited

U.S. PATENT DOCUMENTS

| | | | |
|---|---|---|---|
| 4,130,714 | 12/1978 | Sarges | 548/389 |
| 4,864,028 | 9/1989 | York, Jr. | 546/15 |
| 5,151,544 | 9/1992 | DuPriest et al. | 560/10 |

OTHER PUBLICATIONS

Ariens, "Nonchiral, Homochiral and Composite Chiral Drugs" *Trends in Pharmacologica Sciences* 14:68–G35172 5 (Feb. 1993).
DuPriest, et al., "Spiro[fluoreneisothiazolidin]one Dioxides: New Aldose Reductase and L–Hexonate Dehydrogenase Inhibitors" *J. Med. Chem* 34:3229–3234 (1991).
Cholerton et al., "The role of individual human cytochromes P450 in drug metabolism and clinical response," TiPS, 13:434–439 (1992).
Drayer, "Pharmacodynamic and pharmacokinetic differences between drug enantiomers in humans: An overview," Clin. Pharmacol. Ther., 40:125–133 (1986).
Kiss et al., "Oxidation of Aldose Reductase Inhibitors AL0–4114 and AL0–3152 Catalyzed by Liver Microsomes," Drug Metabolism and Disposition, 20:948–953 (1992).
Park et al., "Comparison of the Pharmacokinetics and Pharmacodynamics of the Aldose Reductase Inhibitors, AL03152 (RS), AL03801 (R), and AL03803 (S)," Pharm. Res., 10:593–597 (1993).
Sarges et al., "Synthesis of Optically Active Spirohydantoins by Asymmetric Induction. Hydantoin Formaton from Amino Nitriles and Chlorosulfonyl Isocyanate," J. Org. Chem., 47:4081–4085 (1982).
DeCamp, "The FDA Perspective on the Development of Stereoisomers," *Chirality* 1:2–6(1989).
Tobert et al., "Enhancement of uricosuric properties of indacrinone by manipulation of the enantiomer ratio," *Clin. Pharmacol. Ther.*, 29(3):344–350 (1981).

*Primary Examiner*—Marianne M. Cintins
*Assistant Examiner*—Keith MacMillan
*Attorney, Agent, or Firm*—James A. Arno; Barry L. Copeland

[57] ABSTRACT

Disclosed are novel compositions comprising mixtures useful to treat the metabolically impaired and to improve patient compliance. Included are non-racemic mixtures of certain chiral spirofluorenehydantoins. Methods of use to treat glucose toxicity and complications arising from diabetes mellitus are also disclosed.

18 Claims, No Drawings

COMPOSITIONS AND METHODS FOR THE TREATMENT OF THE METABOLICALLY IMPAIRED AND FOR IMPROVED COMPLIANCE

BACKGROUND OF THE INVENTION

1. Field of the Invention

This invention relates to novel compositions useful in the treatment of metabolically impaired patients and in promoting enhanced patient compliance. Within the scope of the invention are non-racemic mixtures of certain chiral spirofluorenehydantoins, which may be used to prevent glucose toxicity arising from the intracellular reduction of glucose to sorbitol. More specifically, the compositions of this invention may be used in the treatment of sequelae of neuropathy, cataract vasculopathies, retinopathy and other complications arising from diabetes mellitus. The invention also relates to methods of treatment using such compositions.

2. Description of Related Art

Subsequent to administration, many commonly prescribed drugs undergo metabolic oxidation brought about by various oxidative agents normally produced by the body. Some patients, however, because of their genetic make-up, may fail to produce sufficient amounts of the necessary metabolizing agent(s). Others may have a frank deficiency or dysfunction of drug metabolizing tissue due to hepatitis, alcoholism or other chronic disease. In either case, such patients will be referred to as "metabolically impaired" or a "poor drug metabolizer." Patients with substantially normal metabolic capabilities are referred to as "extensive metabolizers."

Certain chronic disease patients, such as diabetes mellitus patients, can be at significant risk during drug therapy if they are poor drug metabolizers. They exhibit impaired drug metabolism because of genetic predisposition, liver/kidney disease, obesity, advanced age, or a combination of two or more of these factors. Liver and kidney damage, respectively, may occur as a result of cirrhosis associated with chronic pancreatitis and chronic hyperglycemia in the diabetic patient. However, liver cirrhosis might also arise due to alcoholism, hepatitis, etc., which are not diabetic sequelae. It follows that an alcoholic or diabetic patient with advanced kidney and liver disease, who is also genetically a poor drug metabolizer, is at extreme risk of drug toxicity.

Even an otherwise healthy diabetic patient can be a poor drug metabolizer when that subject cannot genetically express a particular drug metabolizing enzyme. This defect can have clinical significance when it slows drug intermediary metabolism, detoxification and disposition. This slowing can cause drug accumulation and a toxicity which resembles a drug overdose. In addition, this drug accumulation can cause the production of abnormal intermediary metabolites which can result in other insidious toxic side-effects. In summary, certain drugs with narrow therapeutic indices can become acutely toxic, even fatal, while others may cause longer term side-effects.

Nevertheless, a drug at a fixed dose has historically been used to serve the therapeutic needs of a broad spectrum of patients without regard to their metabolic status. Consequently, patients with metabolic limitations have occasionally suffered adverse reactions due to toxic drug accumulation. An understanding of the particular patient's drug metabolizing ability will facilitate more appropriate prescribing. Increasingly it is possible to predict the drug metabolizing ability of a patient and this will in certain instances permit selection of a safe drug dosage for that individual. However, a short-acting drug which might be selected for the safety of poor metabolizers will ordinarily require daily multi-dosing in the extensive metabolizer to provide equivalent therapeutic benefit. In chronic disease therapy, these multi-dose per day drugs often fail because of patient noncompliance to self-medicate. Consequently, because most patients are extensive metabolizers, there is a bias favoring relatively longer acting drugs, which may not be well tolerated by poor metabolizers.

With respect to diabetes mellitus, racemic mixtures and the R and S enantiomers of certain chiral spirofluorenehydantoins have previously been reported to be aldose reductase inhibitors and thus of value in controlling complications arising from that disease (e.g., diabetic cataracts and neuropathy). Reference is made to commonly assigned U.S. Pat. No. 4,864,028 (York) for further background in this regard. The entire contents U.S. Pat. No. 4,864,028 relating to the utility, structure and synthesis of such chiral spirofluorenehydantoins are hereby incorporated in the present specification by reference.

Examples of enantiomers of a given compound having different degrees of pharmacokinetic or pharmacodynamic properties are known to those skilled in the art. See, e.g., Drayer, D. E., *Clin. Pharmacol. Ther.* 40:125–133 (1986). In the case of aldose reductase inhibitors, certain enantiomers have been described as having significantly greater inhibitory activity than their antipodes. See, e.g., U.S. Pat. No. 4,130,714.

Methods of obtaining enantiomerically pure forms of chiral hydantoins have been described previously. Conventional methods have involved resolution using the resolving agent brucine, or asymmetric synthesis using a method similar to a procedure described in Sarges, et al., *J. Org. Chem.*, 47:4081 (1982). Such methods may, however, be unsatisfactory in achieving complete resolution of certain substituted spirofluorenehydantoins, such as 2,7-difluoro-4-methoxyspiro[9H-fluorene-9,4'-imidazolidine]-2',5'-dione. A method for synthesizing the pure R and S enantiomers of such spirofluorenehydantoins is described in commonly assigned U.S. Pat. No. 5,151,544 (DuPriest et al.). To the extent such compounds are susceptible to enantiomeric resolution or asymmetric synthesis, the more active enantiomer would typically be favored as a therapeutic agent, provided that its negative side-effects are not disproportionately greater than those of its antipode.

Thus, there is a need for compositions and methods which benefit the metabolically impaired patient and provide for more convenient dosing regimens for both poor and extensive metabolizers. The present invention teaches, inter alia, compositions and methods responsive to this need.

SUMMARY OF THE INVENTION

It has been found that certain drugs will exhibit comparable therapeutic activity in vitro, but significantly different metabolic half-lives in vivo. Described herein are therapeutic agents having optical isomers, or enantiomers, which meet this criterion. A proper mixture of enantiomers, as described in the instant invention, can benefit patients who are poor drug metabolizers, by avoiding a potentially toxic drug accumulation. A tailored mixture of such enantiomers can also benefit extensive metabolizers by providing an improved dosing regimen. Patient compliance is improved when the enantiomeric mixture is tailored to provide a convenient dosing regimen (e.g., once or twice daily dosage)

for either poor or extensive metabolizers. This is especially true for self-medicating patients. The resulting enhanced compliance should maximize the drug's therapeutic benefit to the patient.

Among diabetics, it has been found that a non-racemic mixture of the enantiomers of certain spirofluorenehydantoins can be selected to control drug serum half-life and concentration and to provide once or twice a day dosing in either the poor or extensive drug metabolizing diabetic patients. In a relatively healthy diabetic who is an extensive drug metabolizer, the metabolic disposition of a non-racemic mixture of a drug enriched with a short metabolic half-life enantiomer will be significantly shorter than in a diabetic patient who is a poor metabolizer. With poor metabolizers, it will be preferable to use a drug with a facile metabolism and elimination over a drug with a longer metabolic half-life. The non-racemic mixture enriched with the shorter half-life enantiomer, as described herein, will be the desired choice of a metabolically impaired diabetic patient. Therefore, one can select a non-racemic mixture for use in diabetics who are poor metabolizers who might have advanced liver and/or kidney disease, and likewise provide another mixture for the relatively healthy diabetic who is an extensive drug metabolizer. Each mixture is designed to be safe and effective for each of the targeted diabetic patient populations.

Another advantage of a non-racemic mixture is that it in addition to controlling drug pharmacokinetics, it permits control of manufacturing cost. The non-racemic mixture of an aldose reductase inhibitor drug of the present invention should cost substantially less than the pure enantiomer while performing as well as or better than such pure enantiomer.

It has surprisingly been found that the R and S enantiomers of certain spirofluorenehydantoins, including 2,7-difluoro-4-methoxyspiro[9H-fluorene-9,4'-imidazolidine]-2',5'-dione, possess similar inhibitory activities against aldose reductase and L-hexonate dehydrogenase, but exhibit markedly different pharmacokinetics.

The present invention includes novel compositions comprising a mixture of drugs which exhibit comparable aldose reductase inhibitory activity in vitro, but significantly different metabolic half-lives in vivo. The compositions may contain non-racemic mixtures of the R and S enantiomers of chiral spirofluorenehydantoins of the following structure:

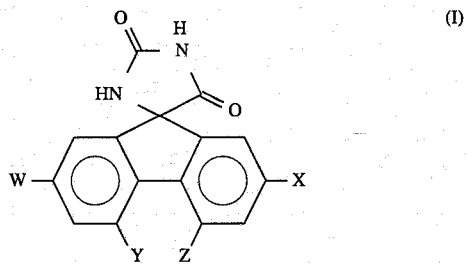

wherein: W and X are each, independently of the other, selected from the group consisting of hydrogen, chloro and fluoro; one of Y and Z is selected from the group consisting of methyl, methoxyl and methylthio and the other is selected from the group consisting of hydrogen, chloro and fluoro; and pharmaceutically acceptable salts thereof.

Unexpectedly, it has been discovered that non-racemic mixtures of the enantiomers of compounds of formula I may possess pharmacokinetic properties that are significantly different from either the racemic mixture or the pure enantiomers. Specifically, it has been found that differences in the metabolic half-lives of the enantiomers of the present invention make possible dosaging, using non-racemic mixtures thereof, which permits greater initial potency with less risk of adverse side effects associated, for example, with a toxic threshold.

DETAILED DESCRIPTION OF THE INVENTION

The present invention contemplates compositions comprising mixtures of two or more agents having comparable activity, but different metabolic half-lives, together with methods of treatment using such compositions. The term "comparable activity" means not more than a five fold difference in in vitro activity. With respect to enzyme inhibition, such as aldose reductase inhibition, this means that the $IC_{50}$ value of one agent cannot exceed that of any other by more than a factor of 5. The $IC_{50}$ values (inhibitor concentration producing 50% inhibition of the enzyme activity) may be determined in the manner described in Example 1 below. The term "different metabolic half-lives" means that there is at least a 25% difference between the metabolic half-lives of the agents in the metabolic phase (initial distribution, disposition or terminal elimination) primarily responsible for the disposition of the drug at plasma steady state. For the spirofluorenehydantoin aldose reductase inhibitors of the present invention, the $t_{1/2\beta}$ value of one agent must be greater than the other by a factor of at least 1.25. The $t_{1/2\beta}$ values (disposition phase half-life) may be determined in the manner described in Example 2 below.

The compositions of this invention may be used to prevent glucose toxicity arising from the reduction of glucose to sorbitol in certain patients. The preferred use is in the treatment of complications arising from diabetes mellitus. Preferably, the customized mixtures would be related to the therapeutic needs and/or metabolic limitations of a given patient. Such needs or limitations may be assessed in the manner normally practiced by those skilled in the art to determine abnormal blood chemistry arising from drug toxicity or blood drug level. After determining such therapeutic needs and/or metabolic limitations, a suitable, therapeutically effective amount of the customized mixture can be administered in the ordinary manner. The ratio of the shorter and longer acting components of the mixtures of the present invention may range from about 0.05:1 to about 20:1.

Such customized mixtures afford patients, especially diabetic humans, a means for more convenient dosing (e.g. once or twice a day) while improving metabolic safety in those who suffer liver dysfunction and/or other metabolic abnormalities interfering with normal metabolic disposition of therapeutic agents. The preferred combination of the drugs will depend upon the condition and specific needs of the particular patient. In a metabolically impaired patient, a combination containing predominantly the shorter acting drug is indicated.

Therapeutic agents having optical isomers, or enantiomers, which meet the foregoing criteria are preferred. One unexpected discovery of the present invention is that the enantiomerically pure forms of certain spirofluorenehydantoins may exhibit similar activity in vitro, but possess significantly different half lives in vivo, resulting in marked pharmacokinetic differences. Applicant has further discovered that by combining such enantiomerically pure compounds in different proportions, one can create customized mixtures which yield either longer or shorter half-lives than the racemic mixture. Enantiomerically pure forms of the compounds of formula I may be prepared in accordance with the method described in U.S. Pat. No. 5,151,544. Once prepared, the pure enantiomers of a given spirofluorenehydantoin may be mixed in the desired ratio to yield a non-racemic, i.e. other than 1:1 mixture. Alternatively, either enantiomerically pure component may be mixed with the respective racemate to yield a non-racemic mixture having the desired ratio of R and S enantiomers. The enantiomers may be mixed in dry form or first placed in solution in a suitable liquid carrier and then mixed. In a preferred approach, a partial resolution of the racemate may be effected chromatographically to yield the non-racemic mixture. Such partial resolution may be achieved by use of a semipreparative column packed with a chiral solid. An ULTRON ES-OVM column using methanol/water (27/73, v/v), $5 \times 10^{-3}$M in KHPO$_4$ with detection at $\lambda$=270 nm is preferred.

Combinations of the R-(+) and S-(-) enantiomers of 2,7-difluoro-4-methoxyspiro[9H-fluorene-9,4'-imidazolidine]-2',5'-dione are preferred for purposes of this invention. The ratios favoring the shorter half-life S-(-) enantiomer of the spirofluorenehydantoin over the R-(+) enantiomer may range from about 1.5:1 to about 20:1. Preferably, the concentration of the more rapidly metabolized S-(-) enantiomer will exceed that of the more persistent R-(+) enantiomer in ratios from about 2:1 to about 9:1; most preferably in ratios of about 3:1.

Appropriate dosing will depend upon the particular needs and the physical condition of a given patient. Typical doses will be from 1 to 50 mg of the non-racemic mixture, taken or administered once or twice a day.

As will be appreciated by those skilled in the art, the compositions may be formulated in various dosage forms suitable for either systemic or topical delivery, including tablets, capsules, solutions, suspensions, emulsions, gels, and erodible solid ocular inserts. The systemic compositions are preferably dry, in tablet form. In addition to the above-described non-racemic mixtures, which comprise the principal active ingredients, the compositions of the present invention may further comprise various formulatory ingredients conventionally employed by those skilled in the art.

In a topical formulation, antimicrobial preservatives and tonicity agents may be required. Examples of suitable antimicrobial preservatives include: benzalkonium chloride, thimerosal, chloro-butanol, methyl paraben, propyl paraben, phenylethyl alcohol, edetate disodium, sorbic acid, ONAMER M and other agents equally well known to those skilled in the art. Such preservatives, if utilized, will typically be employed in an amount of from about 0.001% to 0.5% by weight (wt. %). Examples of suitable agents which may be utilized to adjust the tonicity or osmolality of the formulations include sodium chloride, potassium chloride, mannitol, dextrose, glycerine and propylene glycol. Such agents, if utilized, will be employed in an amount of about 0.1% to 10.0% by weight (wt. %).

The compositions and methods of treatment of the present invention are further illustrated by the following examples, wherein specific embodiments of the invention are described in detail. However, it should be understood that the invention is not limited to the specific details of these examples.

EXAMPLE 1

The in vitro inhibiting activity of racemic 2,7-difluoro-4-methoxyspiro[9H-fluorene-9,4'-imidazolidine]-2',5'-dione, prepared in accordance with U.S. Pat. No. 4,864,028 (hereafter referred to as "A($\pm$)") was compared to that of the R(+) and S(-) enantiomers thereof, prepared in accordance with U.S. Pat. No. 5,151,544 (referred to hereafter as "A(+)" and "A(-)", respectively), with respect to aldose reductase and L-hexonate dehydrogenase.

The test methods used for measuring in vitro inhibition activities of these compounds toward aldose reductase and L-hexonate dehydrogenase are known. The method utilized for measuring the inhibition of aldose reductase is described in B. W. Griffin and L. G. McNatt, "Characterization of the Reduction of 3-Acetylpyridine Adenine Dinucleotide Phosphate by Benzyl Alcohol Catalyzed by Aldose Reductase", Arch. Biochem, Biophys. 246:75–81 (1986). The method utilized for measuring the inhibition of L-hexonate dehydrogenase is described in M. T. DuPriest, B. W. Griffin, D. Kuzmich, and L. G. McNatt "Spiro[fluoreneisothiazolidin] one Dioxides: New Aldose Reductase and L-Hexonate Dehydrogenase Inhibitors", J. Med Chem. 34:3229–3234 (1991). Both methods are based on detection of the rate of increase of fluorescence of NADPH (reduced form of nicotinamide adenine dinucleotide phosphate) or an analog, formed as a product of the enzymatic reaction, i.e., oxidation of an appropriate alcohol substrate by the respective oxidized pyridine species. In the assay for aldose reductase, the reaction mixture contained 50 mmol/L potassium phosphate buffer (pH 7.5), 12 mmol/L benzyl alcohol, 12 µmol/L oxidized 3-acetylpyridine adenine dinucleotide phosphate, and rat lens supernatant fraction (50–100 µg total protein) in a total volume of 1.0 mL. The assay for L-hexonate dehydrogenase consisted of the following components: 50 mmol/L potassium phosphate buffer (pH 7.5), 20 mmol/L L-gulonate, 25 µmol/L NADP+, and rat kidney supernatant fraction (50–100 pg total protein) in a total volume of 1.0 mL. The enzyme-dependent rate of formation of the reduced pyridine nucleotide was monitored with a fluorescence spectrophotometer set at excitation/emission wavelengths of 365/480 nm for the NADP+analog and 365/465 nm for NADP+; slit widths were routinely set at 10 nm. Reactions were carried out at room temperature; blank rates with one component of the reaction omitted were typically less than 10% of the rate of the complete reaction.

The IC$_{50}$ values (inhibitor concentration producing 50% inhibition of the reaction under the standard assay conditions described) were computed by linearregression analysis of the linear portion of the dose-response curve for each inhibitor. The reliability of the data was assured by the following procedures: (1) using the same amount of enzyme activity for all inhibitors; (2) demonstrating that each activity could be inhibited completely by a moderate concentration of a potent inhibitor (standard); (3) evaluating the activity of a known inhibitor each day; and (4) generating characteristic, reproducible inhibition plots for individual inhibitors.

The activities of each of the pure enantiomers and the racemic mixture are demonstrated in the following table: Inhibition of Rat Aldose Reductase (AR) and L-Hexonate Dehydrogenase (L-HDH)

| Compound | IC$_{50}$ µMol/L ($\pm$ SEM) | |
| --- | --- | --- |
| | Rat AR | Rat L-HDH |
| A($\pm$) | 5.7 $\pm$ 1.7 (n = 4) | 2.2 $\pm$ 0.9 (n = 3) |
| A(+) | 5.5 $\pm$ 0.2 (n = 3) | 3.0 $\pm$ 0.4 (n = 2) |
| A(-) | 5.9 $\pm$ 0.3 (n = 3) | 3.0 $\pm$ 0.4 (n = 2) |

The foregoing demonstrates that A(+) and A(-) exhibit no significant difference in activity in vitro.

EXAMPLE 2

The pharmacokinetic properties of A(±) of Example 1 were compared with those of each enantiomer, A(+) and A(−) of Example 1. The comparison was made in rats following an intravenous bolus injection.

The test articles were formulated in a 0.1N sodium carbonate solution to yield a 2 mg/mL solution. A total of 126 male Sprague-Dawley rats weighing 200–300 g were divided into three groups of 42 rats each. The animals were offered food and water ad libitum except fasting overnight prior to and for four hours after dosing. Rats in each group received a single 2 mg/kg intravenous dose of A(+) or A(−) or A(±) via the tail vein. At the following times postdose, three rats from each group were anesthetized by carbon dioxide inhalation and plasma samples were collected from each animal: 0, 1, 4, 8, 24, 31, 48, 72, 96, 120, 144, 168, 216, and 336 hours. Plasma concentrations of each drug were determined by gas chromatographic-electron capture (GC-EC) methods known to those skilled in the art, with a lower limit of detection of 2 ng/mL. See, e.g., Park, Y. H., et al., *Xenobiotica* 22:543–550 (1992). The values of the elimination rate constants, $\alpha, \beta$ and $\gamma$, were obtained by linear regression analysis of the log-linear portion of the plasma concentration-time curve. These constants correspond to the initial distribution, disposition and terminal elimination phases, respectively. The $\alpha$ and $\beta$ values were obtained by the method of residuals. The corresponding half-lives ($t_{1/2}\alpha$, $t_{1/2}\beta$ and $t_{1/2}\gamma$) were calculated by dividing 0.693 by each respective parameter. The area under the plasma concentration versus time curve from 0 to infinity (AUC.∞) was calculated by linear trapezoidal summation with extrapolation to infinity. Total plasma clearance $CL_T$ was calculated as dose divided by AUC.∞. The area under the first moment curve (AUMC) is the area under the curve observed for the product of time and concentration, versus time. Apparent volume of distribution at steady state (Vss) was calculated by the product of dose and AUMC, divided by $(AUC.\infty)^2$.

The mean plasma concentration versus time data for A(+), A(−) and A(±) following a 2 mg/kg intravenous bolus injection in rats and the pharmacokinetic parameters calculated from the data are presented in the following table:

Mean Plasma Concentrations and Pharmacokinetic Parameters in Rats Following a 2 mg/kg Intravenous Bolus Injection

| Time (Hour) | Concentration[a] (µg/mL) | | |
|---|---|---|---|
| | A(+) | A(−) | A(±) |
| 1 | 2.971 ± 0.679 | 7.334 ± 0.220 | 5.078 ± 0.441 |
| 4 | 2.362 ± 0.456 | 3.797 ± 0.975 | 3.593 ± 0.441 |
| 8 | 2.362 ± 0.281 | 2.776 ± 0.449 | 2.419 ± 5.444 |
| 24 | 0.486 ± 0.170 | 0.140 ± 0.017 | 0.352 ± 0.034 |
| 31 | 0.382 ± 0.049 | 0.127 ± 0.036 | 0.194 ± 0.022 |
| 48 | 0.162 ± 0.032 | 0.023 ± 0.008 | 0.108 ± 0.027 |
| 72 | 0.067 ± 0.015 | 0.004 ± 0.003 | 0.003 ± 0.004 |
| 96 | 0.033 ± 0.011 | ND | 0.017 ± 0.004 |
| 120 | 0.011 ± 0.004 | ND | 0.013 ± 0.003 |
| 144 | 0.009 ± 0.001 | ND | 0.011 ± 0.002 |
| 168 | 0.005 ± 0.003 | ND | 0.005 ± 0.002 |
| 216 | 0.002 ± 0.001 | ND | 0.002 ± 0.001 |
| 336 | ND | ND | ND |
| $\alpha$ (hour$^{-1}$) | 0.222 | 0.163 | 0.118 |
| $t_{1/2\alpha}$ (hour) | 3.1 | 4.3 | 5.8 |
| $\beta$ (hour$^{-1}$) | 0.048 | 0.081 | 0.085 |
| $t_{1/2\beta}$ (hour) | 14.5 | 8.5 | 8.0 |
| $\gamma$ (hour$^{-1}$) | 0.018 | ND | 0.017 |
| $t_{1/2\gamma}$ (hour) | 37.4 | ND | 40.7 |
| AUC.∞ (µg/hour/mL) | 54.4 | 63.0 | 60.4 |
| AUMC (µg/hour$^2$/mL) | 965 | 402 | 854 |
| $CL_T$ (mL/hour/kg) | 36.7 | 31.7 | 33.1 |
| Vss (L/kg) | 0.59 | 0.17 | 0.47 |

[a]Mean ± SD (N = 3)
ND = Not Detected

The foregoing demonstrates the pharmacokinetic differences of A(+), A(−) and A(±) in rats. A(+) has a triexponential elimination profile with an initial distribution phase, a disposition phase due to metabolism, and a slow terminal elimination phase. A(−), however, lacks a slow terminal elimination phase and has a significantly lower volume of distribution. A(±) has a kinetic profile similar to that of A(+) with the presence of a persistent elimination phase. Thus, while the in vitro activities A(+) and A(−) are not significantly different, their pharmacokinetics are. These pharmacokinetic differences are believed to contribute to the marked differences in the in vivo efficacy of the two enantiomers as demonstrated below.

EXAMPLE 3

To compare the in vivo efficacy of A(±) (from Example 1) and its enantiomers, A(+) and A(−), the $ED_{50}$ values (the effective dose, in mg/kg/day, to achieve 50% inhibition) for inhibition of sorbitol in three tissues (lens, sciatic nerve and retina) of severely diabetic rats, dosed orally for eight days, once a day, were recorded. The results of the foregoing analysis are summarized in the following table:

| Test Compound | $ED_{50}$ mg/kg/day | | |
|---|---|---|---|
| | Lens[1] | S. Nerve | Retina |
| A(+) | 0.15 | 0.08 | 0.15 |
| A(±) | 0.28 | 0.12 | 0.26 |
| A(−) | 1.52 | 1.0 | 2–3 (est.) |

[1]For lens, $ED_{60}$ value is given, because 40% inhibition was the maximum inhibition achieved by (−) at the highest dose (1.5 mg/kg/day).

In all tissues, A(−) was less active than A(+), by a factor of 10 or more. This is believed to be attributable to the faster plasma elimination of A(−). See Example 2 above. A (±) had about 50% of the activity of A (+).

EXAMPLE 4

Customizing the in vivo efficacy of the spirofluorenehydantoin is achieved by mixing a selected quantity of the desired pure enantiomer, A(+) or A(−), with the racemate, A(±), or by partial chromatographic resolution of the racemate, to achieve the desired level of enantiomeric excess. The enantiomeric ratio may be confirmed by optical rotation analysis, as demonstrated by the following table:

| % w/w A(+)isomer | % w/w A(−)isomer | $[\alpha]_D^{25} \pm 0.5°$ | |
|---|---|---|---|
| 90 | 10 | +11.2 | Longer half-life |
| 85 | 15 | +9.8 | |
| 80 | 20 | +8.4 | |

-continued

| % w/w A(+)isomer | % w/w A(−)isomer | $[\alpha]_D^{25} \pm 0.5°$ | |
| --- | --- | --- | --- |
| 75 | 25 | +7.0 | |
| 60 | 40 | +2.8 | ↑ |
| 40 | 60 | −2.8 | ↑ |
| 25 | 75 | −7.0 | |
| 20 | 80 | −8.4 | |
| 15 | 85 | −9.8 | |
| 10 | 90 | −11.2 | Shorter Half Life |

*Calculated values based upon experimental values of
$[\alpha]_D^{25}$ 14° (C = 1, methanol) for A(+)
$[\alpha]_D^{25}$ −14° (C = 1, methanol) for A(−)

as reported in U.S. Pat. No. 5,151,544.

EXAMPLE 5

A dry, solid pharmaceutical composition suitable for oral administration is prepared by mixing the following materials together in the proportions by weight specified:

| | |
| --- | --- |
| A(±) (From Example 1) | 40 |
| A(−) (From Example 1) | 20 |
| Sodium Citrate | 20 |
| Alginic Acid | 5 |
| Polyvinylpyrrolidone | 15 |
| Magnesium Stearate | 5 |

The dry composition is thoroughly blended, tablets are punched from the resulting mixture, each tablet being of such size that it contains 100 mg of the non-racemic spirofluorenehydantoin possessing a ratio of A(−) to A(+) of approximately 2:1. Other tablets are also prepared in a likewise manner containing 10,25 and 200 mg of non-racemic spirofluorenehydantoin, respectively by merely using an appropriate quantity by weight of the non-racemic spirofluorenehydantoin in each case. Likewise other related examples of non-racemic mixtures of the spirofluorenehydantoin can be formulated as tablets on a respective weight proportion by adding either A(−) or A(+) to A(±) to yield tablets possessing ratios of A(−) to A(+) ranging from about 1:20 to about 20:1

EXAMPLE 6

A dry, solid pharmaceutical composition suitable for oral administration is prepared by combining the following materials together in the weight proportions included below:

| | |
| --- | --- |
| A(±) (From Example 1) | 25 |
| A(−) (From Example 1) | 25 |
| Calcium Carbonate | 20 |
| Polyethylene glycol. Average Molecular Weight 25,000 | 30 |

The dried, solid mixture is thoroughly mixed until uniform in composition. The powdered product is then used to fill soft elastic and hard-gelatin capsules so as to provide capsules containing 200 mg of the non-racemic spirofluorenehydantoin in a ratio of A(−) to A(+) of approximately 3:1. Likewise other related examples of non-racemic mixtures of the spirofluorenehydantoin can be formulated as tablets on a respective weight proportion by adding A(−) to A± to yield tablets possessing ratios of A(−) to A(+) ranging from about 1.05:1 to about 20:1.

EXAMPLE 7

A pharmaceutical formulation suitable for topical administration to the human eye is prepared by combining the following materials together in the weight proportions included below.

| | |
| --- | --- |
| A(±) and A(−) in desired non-racemic mixture | 0.05–0.3% |
| Carbomer 934P (or Carbomer 974P) | 0.5% |
| Sodium Chloride | 0.4% |
| Mannitol | 2.4% |
| Disodium Edetate | 0.01% |
| BAC | 0.01% |
| Polysorbate 80 | 0.05% |
| Water for Injection | q.s. |
| Sodium Hydroxide and/or Hydrochloric acid | q.s. |

EXAMPLE 8

A dry, solid pharmaceutical composition suitable for oral administration is prepared by combining the following materials together in the weight proportions included below:

| | |
| --- | --- |
| A(±) (from Example 1) | 34 |
| A(+) (from Example 1) | 16 |
| Calcium Carbonate | 20 |
| Polyethylene glycol. Average Molecular Weight 25,000 | 30 |

The dried, solid mixture is thoroughly mixed until uniform in composition. The powdered product is then used to fill soft elastic and hard-gelatin capsules so as to provide capsules containing 200 mg of the non-racemic spirofluorenehydantoin in a ratio of A(+) to A(−) of approximately 3:1. Likewise other related examples of non-racemic mixtures of the spirofluorenehydantoin can be formulated as tablets on a respective weight proportion by adding A(+) to A(±) to yield tablets possessing ratios of A(+) to A(−) ranging from about 1.05:1 to about 20:1.

EXAMPLE 9

A 1% (w/v) methanol solution of A(±) (from Example 1) is subjected to HPLC on a semipreparative ULTRON ES-OVM column using methanol/water (27/73, v/v), $5 \times 10^{-3}$M in $KHPO_4$ with detection at $\lambda=270$ nm. Under these conditions there will be peak overlap corresponding to A(+) and A(−). The skilled technician will be able to recover fractions encompassing all or part of the overlap phase to yield non-racemic mixtures. Analysis of such fractions by quantitative HPLC using the conditions described above or by optical rotation will confirm the enantiomeric ratio of (A+) and A(−). In this manner, the column may be calibrated and efficient fractionation employed. The partially resolved spirohydantoin may be isolated from solution by evaporation of solvent or by the addition of a nonpolar solvent (e.g. hexane) to precipitate the material. The method of this Example 9 may be employed to prepare the non-racemic mixture components of any of Examples 5 through 8.

The invention has been described herein with reference to certain preferred embodiments. However, as obvious variations thereon will become apparent to those skilled in the art, the invention is not to be considered as limited thereto.

What is claimed is:

1. A pharmaceutical composition useful in the treatment of diabetes mellitus, comprising an amount of a non-racemic spirofluorenehydantoin having first and second enantiomers effective to inhibit aldose reductase, said spirofluorenehydantoin having the structure:

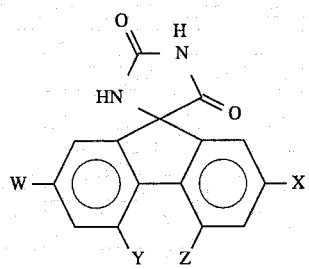

wherein:

W and X are each, independently of the other, selected from the group consisting of hydrogen, chloro and fluoro;

one of Y and Z is selected from the group consisting of methyl, methoxyl and methylthio and the other is selected from the group consisting of hydrogen, chloro and fluoro;

or pharmaceutically acceptable salts thereof; and a pharmaceutically acceptable vehicle therefor; and wherein the ratio of the first enantiomer to the second enantiomer is from about 0.05:1 to about 20:1.

2. The composition of claim 1, wherein the first enantiomer exhibits a metabolic half-life that is significantly shorter than that of the second enantiomer, and wherein the ratio of the first enantiomer to the second enantiomer exceeds 1:1.

3. The composition of claim 1, wherein the spirofluorenehydantoin comprises 2,7-difluoro-4-methoxyspiro[9H-fluorene-9,4'-imidazolidine]-2',5'-dione having a first enantiomer that is R-(+) and a second enantiomer that is S-(−).

4. The composition of claim 3, wherein the concentration of the S-(−) enantiomer exceeds the concentration of the R-(+) enantiomer.

5. The composition of claim 4, wherein the ratio of the S-(−) enantiomer to the R-(+) enantiomer is from about 1.5:1 to about 20:1.

6. A pharmaceutical composition useful in the treatment of diabetes mellitus, comprising a non-racemic mixture of the R-(+) and S-(−) enantiomers of 2,7-difluoro-4-methoxyspiro[9H-fluorene-9,4'-imidazolidine]-2',5'-dione or pharmaceutically acceptable salts thereof, wherein the ratio of said S-(−) enantiomer to said R-(+) enantiomer is from about 2:1 to about 9:1.

7. The composition of claim 6, wherein the ratio of the S-(−) enantiomer to the R-(+) enantiomer is about 3:1.

8. A method of controlling glucose toxicity arising from reduction of glucose to sorbitol in a patient in need of such control, which comprises administering to said patient a therapeutically effective amount of a composition comprising an effective amount of a non-racemic mixture of the R and S enantiomers of a spirofluorenehydantoin of the structure:

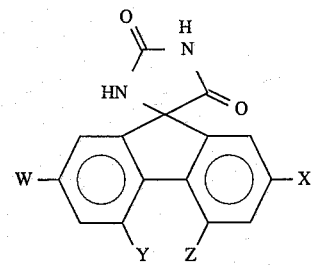

wherein:

W and X are each, independently of the other, selected from the group consisting of hydrogen, chloro and fluoro;

one of Y and Z is selected from the group consisting of methyl, methoxyl and methylthio and the other is selected from the group consisting of hydrogen, chloro and fluoro;

or pharmaceutically acceptable salts thereof; and a pharmaceutically acceptable vehicle therefor.

9. A method according to claim 8, wherein the spirofluorenehydantoin comprises 2,7-difluoro-4-methoxyspiro[9H-fluorene-9,4'-imidazolidine]-2',5'-dione.

10. A method according to claim 8, wherein said glucose toxicity arising from reduction of glucose to sorbitol occurs in a patient with diabetes mellitus.

11. A method according to 8, wherein prior to administering said composition, the patient's metabolic function is assessed and a determination is then made of an acceptable ratio of the R and S enantiomers in the non-racemic mixture and the therapeutically effective amount thereof.

12. A method of treating a patient with complications arising from diabetes mellitus, comprising administering to said patient a therapeutically effective amount of a composition comprising an effective amount of a non-racemic mixture of the R-(+) and S-(−) enantiomers of 2,7-difluoro-4-methoxyspiro[9H-fluorene-9,4'-imidazolidine]-2',5'-dione or pharmaceutically acceptable salts thereof and a pharmaceutically acceptable vehicle therefor.

13. A method according to claim 12, wherein the ratio of the S-(−) enantiomer to the R-(+) enantiomer in the non-racemic mixture is from about 1.5:1 to about 20:1.

14. A method according to claim 13, wherein the ratio of the S-(−) enantiomer to the R-(+) enantiomer in the non-racemic mixture is from about 2:1 to about 9:1.

15. A method according to claim 12, wherein the composition is administered systemically.

16. A method according to claim 15, Wherein the ratio of the S-(−) enantiomer to the R-(+) enantiomer in the non-racemic mixture is about 3:1.

17. A method of treating a medical disorder in a metabolically impaired patient, which comprises administering to said patient a therapeutically effective amount of a composition comprising a non-racemic mixture of an effective amount of a first enantiomer of a therapeutic agent to treat the disorder and an effective amount of a second enantiomer of said therapeutic agent, wherein said first and second enantiomers have comparable in vitro activity, but wherein said first enantiomer has a metabolic half-life in vitro that is significantly shorter than that of said second enantiomer, and wherein the ratio of said first enantiomer to said second enantiomer exceeds 1:1.

18. A method according to claim 17, wherein the metabolic half-life of said second enantiomer exceeds that of said first enantiomer by a factor of at least 1.25.

* * * * *

UNITED STATES PATENT AND TRADEMARK OFFICE
CERTIFICATE OF CORRECTION

PATENT NO. : 5,521,208
DATED : May 28, 1996
INVENTOR(S) : Billie M. York

It is certified that error appears in the above-indentified patent and that said Letters Patent is hereby corrected as shown below:

Column 12, line 56, change "in vitro" to --in vivo--.

Signed and Sealed this

Twentieth Day of March, 2001

Attest:

NICHOLAS P. GODICI

*Attesting Officer*     *Acting Director of the United States Patent and Trademark Office*